United States Patent [19]

Czarniecki et al.

[11] Patent Number: 5,135,915

[45] Date of Patent: Aug. 4, 1992

[54] METHOD FOR THE TREATMENT OF GRAFTS PRIOR TO TRANSPLANTATION USING TGF-$\beta$

[75] Inventors: Christine W. Czarniecki, San Francisco; Michael A. Palladino, Foster City; Eli Shefter, San Francisco, all of Calif.

[73] Assignee: Genentech, Inc., South San Francisco, Calif.

[21] Appl. No.: 258,276

[22] Filed: Oct. 14, 1988

[51] Int. Cl.$^5$ .................... A61K 35/00; A61K 37/02
[52] U.S. Cl. .................... 514/21; 424/85.1; 435/240.1; 435/240.2; 435/240.25; 514/12; 530/399; 604/19; 604/48
[58] Field of Search ............... 514/12, 21; 435/240.2, 435/240.1; 604/48, 19; 530/399; 424/85.1

[56] References Cited

U.S. PATENT DOCUMENTS

| | | | |
|---|---|---|---|
| 4,806,523 | 2/1989 | Bentz et al. | 514/2 |
| 4,886,786 | 12/1989 | Lindstrom et al. | 514/54 |
| 5,055,447 | 10/1991 | Palladino et al. | 514/12 |

FOREIGN PATENT DOCUMENTS

| | | |
|---|---|---|
| 0169016 | 1/1986 | European Pat. Off. |
| 0213776 | 3/1987 | European Pat. Off. |
| 0267463 | 5/1988 | European Pat. Off. |
| 0268561 | 5/1988 | European Pat. Off. |
| 0269408 | 6/1988 | European Pat. Off. |
| 0325471 | 7/1989 | European Pat. Off. |

OTHER PUBLICATIONS

Oates et al., New England J. Med., vol. 319 No. 11 pp. 689–698 (1988).
Ohta et al., Nature, vol. 329 pp. 539–541 (1987).
Hino et al., British J. Haematol., vol. 70 pp. 143–147 (1988).
Kaufman et al., Annals of Surgery, vol. 205 No. 2, pp. 195–198 (1987).
Dibona, American J. Med., vol. 80, Suppl. 1A pp. 12–21 (1986).
Jennings et al., J. Cellular Physiology, vol. 137 pp. 167–172 (1988).
Rosa et al., Science, vol. 239, pp. 783–785 (1988).
Cheifetz et al., Cell, vol. 48, pp. 409–415 (1987).
Segarini et al., J. Biol. Chem., vol. 262, No. 30, pp. 14655–14662 (1987).
Seyedin et al., J. Biol. Chem., vol. 262 No. 5 pp. 1946–1949 (1987).
Roberts et al., Rec. Prog. Hormone Res., vol. 44, pp. 157–196 (1988).
Rizzino, Devel. Biol., vol. 130, pp. 411–422 (1988).
Lyons et al., Eur. J. Biochem., vol. 187 pp. 467–473 (1990).
Sporn et al., J. Cell Biol., vol. 105, pp. 1039–1045 Sep. 1987.
Sampath et al., Proc. Natl. Acad. Sci., vol. 80, pp. 6591–6595 Nov. 1983.
Derynck et al., J. Biol. Chem., vol. 261 No. 10, pp. 4377–4379 1986.
Roberts et al., Biochemistry, vol. 22, pp. 5692–5698, 1983.
Yoshimura et al., Transplant. Proc., vol. 20, No. 2, Suppl. 2, pp. 69–74 Apr. 1988.
McKenna et al., Transplantation, vol 45 No. 1, pp. 76–81, Jan. 1988.
Didlake et al., Transplantation, vol. 45, No. 1, pp. 222–223, Jan. 1988.
Baxter et al., Transplantation Proc., vol. 17, No. 6, Suppl. 4, pp. 112–120, Dec. 1985.
Carel et al., PNAS USA, 87:1591–1595 (1990).
Espevik et al., Chem. Abstr., 107(17):34 (146998f) (1987).
Sporn et al., Science, 233:532–534 (1986).
Bollads et al., Chem. Abstr., 108(3):43–44 (16074m) (1988).
Roberts and Sporn, Adv. in Cancer Res., 51:107, 137–138 (1988).
Chua et al., J. Biol. Chem., 260:5213–5216 (1985).
Brinckerhoff, Arthr. & Rheum., 26:1370–1379 (1983).
Tashijian et al., PNAS USA, 82:4535–4538 (1985).
Roberts & Sporn in Peptide Growth Factors and Their Receptors I, Sporn & Roberts, eds., Springer-Verlag, 1990, pp. 419–472.
Patrick Zuber, "Transforming growth factor $\beta 2$ down-regulates HLA-DR antigen expression on human malignant glioma cells"(1989) Eur. J. Immunol. 1988. 18:1623–1626.
J. H. Kehrl et al., J. Exp. Med. 163: 1037 (1986).
Espenk et al., J. Exp. Med. vol. 166 pp. 571–576 (1987).
H. Ristow, Proc. Nat'l. Acad. Sci. USA 83:5531 (1986).
A. Rook et al., J. Immunol. 136: 3916–3920 (1986).
C. Czarniecki et al., J. Immunol. 140: 4217–4223 (1988).
C. Czarniecki et al., J. Interferon Res. 7: 669 (1987).
M. A. Palladino et al., J. Cell Biochem., Supp. 11A (Jan. 17–Feb. 5, 1987) UCLA Symp. Melcelular & Cellular Bio., A. R. Liss, Inc. NY, Abstrct. A016, p. 10.
Chiu et al., Triennial Symp.: Biology of Growth Factors, Univ. Toronto, Ontario, Canada (Jun. 17–19, 1987).
M. A. Palladino et al., Immunobiology 175: 42 (1987).
M. B. Sporn et al., J. Cell Biol. 105: 1039–1045 (1987).
M. B. Sporn & A. B. Roberts, Nature 332: 217–219 (1988).
A. D. Bollands et al., J. Pharm. Pharmacol. 39: 1021–1024 (1987).
Gamble et al., Science 242: 97–99 (1988).
FDC Report, Sep. 5, 1988, pp. T&G-3-4.

Primary Examiner—Merrell C. Cashion, Jr.
Assistant Examiner—Andrew G. Rozycki
Attorney, Agent, or Firm—Janet E. Hasak

[57] ABSTRACT

A method is provided for the treatment of grafts such as tissue or organs prior to transplantation into a suitable host. The grafts are incubated, coated, or perfused with TGF-$\beta$ for an effective time for the uptake of the agent into the grafts and induction of its biological effects. The thus-treated graft is then transplanted into a compatible host, preferably a human host.

53 Claims, No Drawings

METHOD FOR THE TREATMENT OF GRAFTS PRIOR TO TRANSPLANTATION USING TGF-β

BACKGROUND OF THE INVENTION

This invention relates to the treatment of grafts prior to transplantation into a host. More specifically, this invention is directed to incubating or perfusing a graft such as tissue or an organ with TGF-β and transplanting the treated graft into a suitable recipient.

The success of a transplant of an allograft in a host depends on such factors as the antigens on the transplanted tissue that are recognized by the recipient as foreign and can evoke the rejection response, the cells in the recipient's immune system that mediate rejection, and the reactions that modify either the presentation of the foreign antigen or the cellular response.

The major histocompatibility complex (MHC) is the most important immunogenetic system encoding transplantation antigens. The MHC is genetically complex because it includes many different loci, each encoding separate cell-surface antigens, and because the loci have extensive polymorphism. The loci of the MHC fall into one of two classes, Class I or Class II, based on their tissue distribution, the structure of the expressed antigens, and their functions. Class I antigens, present on all nucleated cells, serve as the primary targets for cytotoxic T (CD8+) lymphocytes. Class II antigens are not distributed in the tissue as widely and serve as primary targets for helper T (CD4+) lymphocytes.

The polymorphic forms of the individual loci of human leukocyte antigen (HLA), the MHC in humans, have been recognized by antibodies and by various in vitro techniques that measure T-lymphocyte recognition. These responses, mediated by the recipient's recognition of polymorphism in the donor, correlate with the strong rejection reactions that take place in vivo.

Investigation into the cellular basis of graft rejection, using both in vitro and in vivo studies, reveals that both CD4+ and CD8+ lymphocytes participate in the rejection response.

Attempts to prolong the survival of allografts and xenografts after transplantation, both in experimental models and in medical practice, have centered mainly on the suppression of the immune apparatus of the recipient. This treatment has as its aim preventive immunosuppression and/or treatment of graft rejection.

Examples of agents used for immunosuppression include cytotoxic drugs, antimetabolites, corticosteroids, and antilymphocytic serum. Nonspecific immunosuppressive agents found particularly effective in preventive immunosuppression (azathioprine, bromocryptine, methylprednisolone, prednisone, and most recently, cyclosporin A) have significantly improved the clinical success of transplantation. The nephrotoxicity of cyclosporin A after renal transplantation has been reduced by coadministration of steroids such as prednisolone, or prednisolone in conjunction with azathioprine. In addition, kidneys have been grafted successfully using anti-lymphocyte globulin followed by cyclosporin A. Another protocol being evaluated is total lymphoid irradiation of the recipient prior to transplantation followed by minimal immunosuppression after transplantation.

Treatment of rejection has involved use of steroids, 2-amino-6-aryl-5-substituted pyrimidines, heterologous anti-lymphocyte globulin, and monoclonal antibodies to various leukocyte populations, including OKT-3. See generally *J. Pediatrics*, 111: 1004–1007 (1987), and specifically U.S. Pat. No. 4,665,077.

The principal complication of immunosuppressive drugs is infections. Additionally, systemic immunosuppression is accompanied by undesirable toxic effects (e.g., nephrotoxicity when cyclosporin A is used after renal transplantation) and reduction in the level of the hemopoietic stem cells. Immunosuppressive drugs may also lead to obesity, poor wound healing, steroid hyperglycemia, steroid psychosis, leukopenia, gastrointestinal bleeding, lymphoma, and hypertension.

In view of these complications, transplantation immunologists have sought methods for suppressing immune responsiveness in an antigen-specific manner (so that only the response to the donor alloantigen would be lost). Such specific immunosuppression generally has been achieved by modifying either the antigenicity of the tissue to be grafted or the specific cells capable of mediating rejection. In certain instances, whether immunity or tolerance will be induced depends on the manner in which the antigen is presented to the immune system. Pretreating the allograft tissues by growth in tissue culture before transplantation has been found in two murine model systems to lead to permanent acceptance across MHC barriers. Lafferty et al., *Transplantation*, 22: 138–149 (1976); Bowen et al., *Lancet*, 2:585–586 (1979). It has been hypothesized that such treatment results in the depletion of passenger lymphoid cells and thus the absence of a stimulator cell population necessary for tissue immunogenicity. Lafferty et al., *Annu. Rev. Immunol.*, 1: 143 (1983). See also Lafferty et al., *Science*, 188: 259–261 (1975) (thyroid held in organ culture) and Gores et al., *J. Immunol.*, 137: 1482–1485 (1986) and Faustman et al., *Proc. Natl. Acad. Sci. U.S.A.*, 78: 5156–5159 (1981) (islet cells treated with murine anti-Ia antisera and complement before transplantation). Also, thyroids taken from donor animals pretreated with lymphocytotoxic drugs and gamma radiation and cultured for ten days in vitro were not rejected by any normal allogeneic recipient. Gose and Bach, *J. Exp. Med.*, 149: 1254–1259 (1979). All of these techniques involve depletion or removal of donor lymphocyte cells.

In some models such as vascular and kidney grafts, there exists a correlation between Class II matching and prolonged allograft survival, a correlation not present in skin grafts. Pescovitz et al., *J. Exp. Med.*, 160:1495–1508 (1984); Conti et al., *Transplant. Proc.*, 19:652–654 (1987). Therefore, donor-recipient HLA matching has been utilized. Additionally, blood transfusions prior to transplantation have been found to be effective. Opelz et al., *Transplant. Proc.*, 4: 253 (1973); Persijn et al., *Transplant. Proc.*, 23: 396 (1979). The combination of blood transfusion before transplantation, donor-recipient HLA matching, and immunosuppression therapy (cyclosporin A) after transplantation was found to improve significantly the rate of graft survival, and the effects were found to be additive. Opelz et al., *Transplant. Proc.*, 17: 2179 (1985).

The transplantation response may also be modified by antibodies directed at immune receptors for MHC antigens. Bluestone et al., *Immunol. Rev.* 90:5–27 (1986). Further, graft survival can be prolonged in the presence of antigraft antibodies, which lead to a host reaction that in turn produces specific immunosuppression. Lancaster et al., *Nature*, 315:336–337 (1985).

The immune response of the host to MHC antigens may be modified specifically by using bone marrow transplantation as a preparative procedure for organ grafting. Thus, anti-T-cell monoclonal antibodies are used to deplete mature T cells from the donor marrow inoculum to allow bone marrow transplantation without incurring graft-versus-host disease. Mueller-Ruchholtz et al., *Transplant Proc.*, 8:537–541 (1976). In addition, elements of the host's lymphoid cells that remain for bone marrow transplantation solve the problem of immunoincompetence occurring when fully allogeneic transplants are used.

The survival time of skin grafts has been prolonged by a factor of two by treatment in vitro with cortisone, thalidomide, or urethane before implantation into a laboratory animal. The amount of drug locally applied to the skin was smaller than the amount required to achieve a similar effect by injecting the drug systemically. In an additional study, the donor skin was treated in vitro with streptokinase/streptodornase, or with RNA and DNA preparations of the recipient. Further, treatment of transplant tissues with a solution of glutaraldehyde prior to transplantation was found to reduce their antigenicity. See U.S. Pat. No. 4,120,649.

The transforming growth factor-$\beta$ (TGF-$\beta$) molecules identified thus far are each dimers containing two identical 112 residue polypeptide chains linked by disulfide bonds. The molecular mass of these dimers is about 25 kd. Biologically active TGF-$\beta$ has been defined as a molecule capable of inducing anchorage-independent growth of target cell lines or rat fibroblasts in in vitro cell culture, when added together with EGF or TGF-$\alpha$ as a co-factor. TGF-$\beta$ is secreted by virtually all cell types in an inactive form. This latent form is first activated by proteolytic cleavage of mature TGF-$\beta$ from its precursor (at the Arg-Ala bond in position 278). A non-covalent complex is formed from the association of the mature TGF-$\beta$ with the precursor remainder. This complex is disrupted so as to activate the TGF-$\beta$ either by exposure to transient acidification or by the action of exogenous proteases.

There are at least three forms of TGF-$\beta$ currently identified, TGF-$\beta_1$, TGF-$\beta_2$, and TGF-$\beta_3$. Suitable methods are known for purifying this family of TGF-$\beta$s from platelets or placenta, for producing it in recombinant cell culture, and for determining its activity. See, for example, R. Derynck et al., *Nature*, 316:701 (1985) and U.S. Ser. Nos. 715,142; 500,832; 500,833, all abandoned; European Pat. Pub. Nos. 200,341 published Dec. 10, 1986, 169,016 published Jan. 22, 1986; 268,561 published May 25, 1988; and 267,463 published May 18, 1988; U.S. Pat. No. 4,774,322; Seyedin et al, *J. Biol. Chem.*, 262: 1946–1949 (1987); Cheifetz et al, *Cell*, 48: 409–415 (1987); Jakowlew et al., *Molecular Endocrin.*, 2: 747–755 (1988); and Dijke et al., *Proc. Natl. Acad. Sci. U.S.A.*, 85: 4715–4719 (1988), the entire contents of these publications being expressly incorporated by reference.

TGF-$\beta$ has been shown to have numerous regulatory actions on a wide variety of both normal and neoplastic cells. Recent studies indicate an important role for TGF-$\beta$ in cells of the immune system (J. Kehrl et al., *J. Exp. Med.*, 163:1037 [1986]; H-J. Ristow, *Proc. Natl. Acad. Sci. U.S.A.*, 83:5531 [1986]; A. Rook et. al., *J. Immunol.*, 136:3916 [1986]) and in proliferation of connective and soft tissue for wound healing applications (M. Sporn et al., *Science*, 219:1329 [1983]; R. Ignotz et al., *J. Biol. Chem.*, 261:4337 [1986]; J. Varga et al., *B. B. Res. Comm.*, 138:974 [1986]; A. Roberts et al., *Proc. Natl. Acad. Sci. U.S.A.*, 78:5339 [1981]; A. Roberts et al., *Fed. Proc.*, 42:2621 [1983]; A. Roberts et al., *Proc. Natl. Acad. Sci. U.S.A.*, 83:4167 [1986]; U.S. Ser. No. 500,833, supra; U.S. Pat. No. 4,774,228 to Seyedin et al.), as well as epithelia (T. Matsui et al., *Proc. Natl. Acad. Sci. U.S.A.*, 83:2438 [1986]; G. Shipley et al. *Cancer Res.*, 46:2086 [1986]). Moreover, TGF-$\beta$ has been described as a suppressor of cytokine (e.g., IFN-$\gamma$, TNF-$\alpha$) production, indicating its use as an immunosuppressant for treating inflammatory disorders (Espevik et al., *J. Exp. Med.*, 166: 571–576 [1987]; European Pat. Pub. Nos. 269,408 published Jun. 1, 1988 and 213,776 published Mar. 11, 1987), and as a promoter of cachexia (Beutler and Cerami, *New Eng. J. Med.*, 316: 379 [1987]). Further, TGF-$\beta$ induces collagenase secretion in human fibroblast cultures (Chua et al., *J. Biol. Chem.*, 260:5213–5216 [1983]); stimulates the release of prostaglandins and mobilization of calcium (A. Tashjian et al., *Proc. Natl. Acad. Sci.* U.S.A., 82:4535 [1985]); and inhibits endothelial regeneration (R. Heimark et al., *Science*, 233:1078 [1986]).

TGF-$\beta$ is multifunctional, as it can either stimulate or inhibit cell proliferation, differentiation, and other critical processes in cell function (M. Sporn, *Science*, 233:532 [1986]).

The multifunctional activity of TGF-$\beta$ is modulated by the influence of other growth factors present together with the TGF-$\beta$. TGF-$\beta$ can function as either an inhibitor or an enhancer of anchorage-independent growth, depending on the particular set of growth factors, e.g., EGF or TGF-$\alpha$, operant in the cell together with TGF-$\beta$ (Roberts et al., *Proc. Natl. Acad. Sci.* U.S.A., 82:119 [1985]). TGF-$\beta$ also can act in concert with EGF to cause proliferation and piling up of normal (but not rheumatoid) synovial cells (Brinkerhoff et al., *Arthritis and Rheumatism*, 26:1370 [1983]).

Most recently, TGF-$\beta$ has been found to suppress the expression of Class II histocompatibility antigens on human cells induced by human interferon-$\gamma$ and to inhibit constitutive expression of the Class II antigen message in the cells (Czarniecki et al., *J. Immunol.*, 140: 4217–4223 [1988]; Czarniecki et al. *J. Interferon Res.*, 7: 699 [1987]; Palladino et al., *J. Cell. Biochem.*, Supp. 11A [Jan. 17–Feb. 5, 1987], UCLA Symposia on Molecular and Cellular Biology, Alan R. Liss, Inc., New York, abstract A016, p. 10; Chiu et al., Triennial Symposium: Biology of Growth Factors, University of Toronto, Ontario, Canada, [Jun. 17–19, 1987]; Palladino et al., *Immunobiology*, 175: 42 [1987]).

For a general review of TGF-$\beta$ and its actions, see Sporn et al., *J. Cell Biol.*, 105: 1039–1045 (1987) and Sporn and Roberts, *Nature*, 322: 217–219 (1988).

There is a need in the art for a method to prolong graft survival in transplant operations and minimize the toxicity and other adverse effects arising from the use of large doses of immunosuppressants.

Accordingly, an object of this invention is to provide for longer graft survival in the host.

Another object is to provide for a transplantation method wherein lower amounts of immunosuppressive agents, if any, need be administered to the host to achieve successful results, thereby reducing the side effects associated with systemic administration of immunosuppressive drugs.

These and other objects will become apparent to one of ordinary skill in the art.

SUMMARY OF THE INVENTION

These objects are accomplished by a method for transplanting grafts from donors into hosts which comprises treating a graft with a composition comprising a therapeutically effective amount of TGF-$\beta$; and transplanting the graft into a compatible host.

In another aspect, this invention provides a graft treated with a composition comprising TGF-$\beta$, along or in combination with another immunosuppressive agent.

In a further aspect, this invention provides a composition comprising TGF-$\beta$ in a perfluorochemical emulsion.

The method herein results in grafts that are immunologically stable in the hosts, biologically functional, and capable of being stored prior to transplantation.

This invention enables the establishment of a bank of treated grafts that can be utilized for short-term or long-term storage. In addition, the graft is not rejected when transplanted into suitable hosts. The method is applicable to both allografts and xenografts, and the use of xenografts overcomes the difficulties encountered by the limited supply of tissue from humans.

Description of the Preferred Embodiments

I. Definitions

The term "graft" as used herein refers to biological material derived from a donor for transplantation into a recipient. Grafts include such diverse material as, for example, isolated cells such as islet cells, tissue such as the amniotic membrane of a newborn, bone marrow, hematopoietic precursor cells, and organs such as skin, heart, liver, spleen, pancreas, thyroid lobe, lung, kidney, tubular organs (e.g., intestine, blood vessels, or esophagus), etc. The tubular organs can be used to replace damaged portions of esophagus, blood vessels, or bile duct. The skin grafts can be used not only for burns, but also as a dressing to damaged intestine or to close certain defects such as diaphragmatic hernia. The graft is derived from any source, preferably mammalian, including human, whether from cadavers or living donors.

The term "host" as used herein refers to any compatible transplant recipient. By "compatible" is meant a host that will accept the donated graft. Preferably, the host is mammalian, and more preferably human. If both the donor of the graft and the host are human, they are preferably matched for HLA class II antigens so as to improve histocompatibility.

The term "donor" as used herein refers to the species, dead or alive, from which the graft is derived. Preferably, the donor is mammalian. Human donors are preferably volunteer blood-related donors that are normal on physical examination and of the same major ABO blood group, because crossing major blood group barriers possibly prejudices survival of the allograft. It is, however, possible to transplant, for example, a kidney of a type O donor into an A, B or AB recipient.

The term "transplant" and variations thereof refers to the insertion of a graft into a host, whether the transplantation is syngeneic (where the donor and recipient are genetically identical), allogeneic (where the donor and recipient are of different genetic origins but of the same species), or xenogeneic (where the donor and recipient are from different species). Thus, in a typical scenario, the host is human and the graft is an isograft, derived from a human of the same or different genetic origins. In another scenario, the graft is derived from a species different from that into which it is transplanted, including animals from phylogenically widely separated species, for example, a baboon heart transplanted into a human host.

The term "TGF-$\beta$" refers to the family of molecules described hereinabove. Reference to TGF-$\beta$ herein will be understood to be a reference to any one of the three currently identified forms, TGF-$\beta_1$, TGF-$\beta_2$ and TGF-$\beta_3$, as well as other molecules related to this family of proteins, and those identified in the future, their alleles, and their predetermined amino acid sequence variants, so long as they are effective in the method described herein. The TGF-$\beta$ is appropriately from any source, preferably mammalian, and most preferably human. TGF-$\beta$ from animals other than humans, for example, porcine or bovine sources, can be used for soaking grafts to treat humans. Likewise, if it is desirable to treat other mammalian species such as domestic, farm, sports, or pet animals, human TGF-$\beta$, as well as TGF-$\beta$ from other species, is suitably employed.

The term "immunosuppressive agent" as used herein refers to substances that act to suppress or mask the immune system of the host into which the graft is being transplanted. This would include substances that suppress cytokine production, downregulate or suppress self-antigen expression, or mask the MHC antigens. Examples of such agents include 2-amino-6-aryl-5-substituted pyrimidines (see U.S. Pat. No. 4,665,077, supra, the disclosure of which is incorporated herein by reference), azathioprine (or cyclophosphamide, if there is an adverse reaction to azathioprine); bromocryptine; glutaraldehyde (which masks the MHC antigens, as described in U.S. Pat. No. 4,120,649, supra); antiidiotypic antibodies for MHC antigens; cyclosporin A; one or more steroids, preferably corticosteroids, and most preferably glucocorticosteroids such as prednisone, methylprednisolone, and dexamethasone; anti-interferon-$\gamma$ antibodies; anti-tumor necrosis factor-$\alpha$ antibodies; anti-tumor necrosis factor-$\beta$ antibodies; anti-interleukin-2 antibodies; anti-cytokine receptor antibodies such as anti-IL-2 receptor antibodies; heterologous anti-lymphocyte globulin; pan-T antibodies, preferably OKT-3 monoclonal antibodies; antibodies to CD4; streptokinase; streptodornase; or RNA or DNA from the host.

The preferred agent for this purpose will depend on many factors, including the type of transplantation being performed, as well as the patient's history, but a general overall preference is that the agent be selected from cyclosporin A, a glucocorticosteroid (most preferably prednisone or methylprednisolone), OKT-3 monoclonal antibody, azathioprine, bromocryptine, heterologous anti-lymphocyte globulin, or a mixture thereof.

II. Modes for Carrying Out the Invention

TGF-$\beta$ is appropriately used in its activated form, i.e., the mature form is cleaved from its precursor using a suitable enzyme and the resultant complex is treated with acid, a protease such as plasmin or cathepsin D, alkali, or chaotropic agents, to activate the TGF-$\beta$. See Keski-Oja et al., *J. Cell Biochem. Suppl.*, 11A: 60 (1987); Kryceve-Martinerie et al., *Int. J. Cancer*, 35:553–558 (1985); Lawrence et al., *Biochem. Biophys. Res. Commun.*, 133: 1026–1034 (1985); Lawrence et al., *J. Cell Physiol.*, 121: 184–188 (1984).

The compositions to be used in the therapy herein will be dosed in a fashion consistent with good medical practice taking into account the nature of the transplantation and the disorder to be treated, the species of the host, the medical condition of the individual patient, the presence of any other drug in the composition, and other factors known to practitioners. For purposes herein, the "therapeutically effective amount" of TGF-β used to treat the graft is an amount that is effective to reduce the immunogenicity of the graft so that it will be compatible with the host and not be rejected. A generally effective amount for this purpose is in a range of 1 pg/ml to 1 mg/ml, more preferably, 10 pg/ml to 1 μg/ml, and most preferably, 10 pg/ml to 100 ng/ml, but the practitioner will know more precisely what amount is to be used taking into consideration the factors described above.

The TGF-β is optionally formulated with one or more immunosuppressive agents to enhance the immunosuppressant effect on the graft. The effective amount of such other agents depends on the amount of TGF-β present in the formulation, the type of transplant, and other factors discussed above, but generally also range from about 0.1 pg/ml to 0.5 mg/ml as necessary to achieve the appropriate endpoint, i.e., longer graft survival.

Typically, the TGF-β is formulated by mixing it at ambient temperature at the appropriate pH, and at the desired degree of purity, with physiologically acceptable carriers, i.e., carriers that are non-toxic to recipients at the dosages and concentrations employed. The pH of the formulation depends mainly on the particular use, and concentration of TGF-β, but preferably ranges anywhere from about 3 to about 8. Preferably the TGF-β is maintained at an acidic pH (e.g., about 4 to about 6) to prevent its adhering to the containers in which it is placed, as occurs at pH values approaching physiological levels, and to ensure activation of the TGF-β molecule. Thus, formulation in an acetate buffer at pH 5 is a suitable embodiment. If the TGF-β adheres to the containers in which the grafts are being treated, an appropriate ingredient, such as albumin, is optionally added, in an amount that does not prevent the TGF-β from perfusing or adhering to the graft being treated.

If the TGF-β formulation is to be applied topically, for example, if it is to be painted onto a skin graft prior to transplantation, it is preferable to use a viscous solution such as a gel rather than a non-viscous solution. This may be accomplished, for example, by mixing the solution of the TGF-β with a gelling agent, such as a polysaccharide, preferably a water-soluble polysaccharide, such as, e.g., hyaluronic acid, starches, and cellulose derivatives, e.g., methylcellulose, hydroxyethyl cellulose, and carboxymethyl cellulose. The most preferred gelling agent is methylcellulose. The polysaccharide is generally present in a gel formulation in the range of 1-90% by weight of the gel, more preferably 1-20%. Examples of other suitable polysaccharides for this purpose, and a determination of the solubility of the polysaccharides, are found in EP 267,015, published May 11, 1988, the disclosure of which is incorporated herein by reference.

If the graft to be treated is to be stored for any period of time, the TGF-β is preferably formulated in or added to a perfluorochemical emulsion (acting as a blood substitute) to enable higher concentrations of oxygen to reach the graft. Such emulsions comprise a perfluorochemical such as perfluorodecalin and/or perfluorotripropylamine emulsified with a surfactant in water. Examples of suitable surfactants include the poloxamer surfactants (which represent a series of molecules that are blocked copolymers of ethylene oxide and propylene oxide), alone or in admixture with a phospholipid such as egg lecithin. The perfluorochemical is chosen to be the least toxic in humans. One example of such an emulsion, which is commercially available from Green Cross, is Fluosol-DA 20%, which contains perfluorodecalin and perfluorotripropylamine emulsified with the poloxamer surfactant, Pluronic F-68. The perfluorochemical emulsions and their effects in mammals are described more fully in Bollands et al., *J. Pharm. Pharmacol.*, 39: 1021-1024 (1987), the disclosure of which is incorporated herein by reference.

The TGF-β for use in therapeutic administration is preferably sterile. Sterility is readily accomplished by sterile filtration through (0.2 micron) membranes. TGF-β ordinarily will be stored as an aqueous solution since it is highly stable to thermal and oxidative denaturation, although lyophilized formulations for reconstitution are acceptable.

In accordance with the method of this invention, the graft is contacted with the TGF-β composition. The contact suitably involves incubating or perfusing the organ with the composition or applying the composition to one or more surfaces of the graft. The treatment generally takes place for at least one minute, and preferably from 1 minute to 72 hours, and more preferably from 2 minutes to 24 hours, depending on such factors as the concentration of TGF-β in the formulation, the graft to be treated, and the particular type of formulation. Perfusion is accomplished by any suitable procedure. For example, an organ can be perfused via a device that provides a constant pressure of perfusion having a pressure regulator and overflow situated between a pump and the organ, as described by DD 213,134 published Sep. 5, 1984. Alternatively, the organ is placed in a hyperbaric chamber via a sealing door and perfusate is delivered to the chamber by a pump that draws the fluid from the reservoir while spent perfusate is returned to the reservoir by a valve, as described in EP 125,847 published Nov. 21, 1984.

For skin grafts, the formulation is suitably painted on the lower surface of the skin to be grafted so that there is a layer of the TGF-β between the tissue of the host and the lower surface of the graft. Alternatively, the whole skin graft is submerged in the composition.

After the graft is treated, it is suitably stored for prolonged periods of time or is used immediately in the transplant procedure. Storage life can be enhanced as described above by using a blood substitute in the formulation (e.g., perfluorochemical emulsion), or by perfusing the graft with a formulation of the TGF-β containing chilled isotonic agent and anticoagulant followed by glycerol to allow for freezing of removed organs with no destruction of the cells, as described in JP 60061501 published Apr. 9, 1985. In addition, the organs can be preserved with different liquids that include the formulation while the organs are cooled to freezing temperatures, to preserve the organ semi-permanently without cell necrocytosis, as described by U.S. Pat. Nos. 4,462,215 and 4,494,385.

Respecting cardiac transplants specifically, Parent et al., *Cryobiology*, 18: 571-576 (1981) describes that cold coronary perfusion prior to transplantation at 5° C. increases protection of the homograft during the initial period of implantation. Any of these procedures, or others, are within the scope of this invention if deemed necessary upon or after TGF-β treatment of the graft.

Before transplantation, the graft is preferably washed free of the TGF-β composition, as by soaking it in a physiological saline solution or by other means appropriate for this purpose.

Also, prior to transplantation, the host is optionally given one or more donor-specific blood transfusions to aid in graft survival. An alternative procedure is to subject the host to total lymphoid irradiation prior to the transplantation operation. Any other pre-transplant procedures that would be beneficial to the particular transplant recipient can be performed as part of the method of this invention.

The transplantation procedure itself will depend on the particular disorder being treated, the condition of the patient, etc. The medical practitioner will recognize the appropriate procedure to employ in any given case. The transplants are optionally monitored systematically during the critical postoperative period (the first three months) using any suitable procedure. One such procedure is radionuclide intravenous angiography using 99Tcm-pertechnetate, as described by Thomsen et al., *Acta Radiol.*, 29: 138-140 (1988). In addition, the method herein is amenable to simultaneous, multiple organ perfusion and transplantation (Toledo-Pereyra and MacKenzie, *Am. Surg.*, 46: 161-164 (1980)). After the transplantation, immunosuppression therapy, using TGF-β and/or other immunosuppressant(s), is utilized as necessary to ensure graft survival.

In some instances, it is desirable to modify the surface of the graft so as to provide positively or negatively charged groups, as by using a suitable amino acid or polymer or by attaching a physiologically acceptable source of charged functional groups. For example, a negatively charged surface is appropriate for blood vessels to diminish blood clotting. It also is desirable in certain circumstances to render the surface hydrophobic or hydrophilic by coupling, e.g., phenylalanine, serine or lysine to the surface. An immunosuppressive agent particularly effective for these surface modifications is gluteraldehyde.

Immunosuppression therapy typically involves the administration of an effective amount of an immunosuppressive agent, including TGF-β itself. The immunosuppressive agent compositions will be formulated and dosed in a fashion consistent with good medical practice. Factors for consideration in this context include the clinical condition of the individual patient, the cause of the transplant, the site of delivery of the agent, the method of administration, the scheduling of administration, and other factors known to practitioners. The "effective amount" in this context, which is determined by such considerations, is the minimum amount necessary to prevent an immune response that would result in rejection of the graft by the host. Such amount is preferably below the amount that is toxic to the host or renders the host significantly more susceptible to infections. The amount of immunosuppressive agent required for the invention herein may be lower than that normally required for transplanted grafts that have not been pre-treated, and depends on the individual circumstances surrounding the transplant and the type of immunosuppressive agent employed.

As a general proposition, the total pharmaceutically effective amount of the immunosuppressive agent, cyclosporin A, administered parenterally per dose will be in the range of about 0.1 to 20 mg/kg of patient body weight per day, with the typical range of cyclosporin A currently used in immunosuppressive therapy being 5 to 15 mg/kg/day. For renal transplants it is useful to administer massive doses at short periods of glucocorticosteroid; e.g., methylprednisolone in several-gram doses per day is given for 3 to 5 days followed by 60 to 100 mg prednisone without TGF-β pre-treatment of the graft. With such pre-treatment, lower doses would be expected to be useful.

As noted above, however, these suggested amounts of immunosuppressant are subject to a great deal of therapeutic discretion. The key factor in selecting an appropriate dose and scheduling is the result obtained, i.e., graft survival. For example, relatively higher doses may be needed initially for the treatment of hyperacute graft rejection, which can be attributed to antibody-mediated graft destruction, or at a later stage for the treatment of acute rejection, which is characterized by a sudden decline in graft function.

The immunosuppressive agent is administered by any suitable means, including parenteral, and, if desired for local immunosuppressive treatment, intralesional, administration. Parenteral infusions include intramuscular, intravenous, intraarterial, intraperitoneal, or subcutaneous administration. In addition, the immunosuppressive agent is suitably administered by pulse infusion, particularly with declining doses of the immunosuppressive agent, or by continuous infusion.

The invention will be more fully understood by reference to the following examples. They should not, however, be construed as limiting the scope of the invention. All literature citations are incorporated by reference.

EXAMPLE 1

Murine Skin Graft Model

TGF-β: The TGF-β used herein is from any one of several sources: (1) porcine platelet-derived TGF-$\beta_1$ at 96 percent purity purchased in a lyophilized form and suspended in 4 mM HCl and phosphate buffered saline (PBS) solution prior to use, (2) TGF-$\beta_1$, prepared by recombinant means as described by EP 200,341, supra, (3) TGF-$\beta_2$, prepared as described by U.S. Pat. No. 4,774,322, supra, or (4) TGF-$\beta_3$, prepared by recombinant means as described by EP 267,463, supra (see FIG. 29 and accompanying text of EP 267,463). The TGF-β from any of these sources is recovered and formulated at 100 ng/ml at pH5 in an aqueous acetate buffer. The resultant solution is sterile filtered through a 0.2 micron polysulfone filter.

Grafts: Skin allografts (1×2 cm square) are obtained from BALB/c (H-$2^d$) mice.

Hosts: The hosts used are C57BL/6 (H-$2^b$) mice.

Procedure: The skin grafts are incubated in one of the above TGF-β solutions at room temperature in a sterile glass vial for 1 minute to 24 hours, then washed two times with PBS solution to remove any free TGF-β. The thus-treated skin is applied to the mouse recipient, and covered with vaseline gauze, and then with plaster of Paris, which are removed after ten days. The treated grafts are tightly bound to the recipient. They are initially soft, but become progressively stiffer with minimal shrinkage in size, and remain free from infection. The histology shows that the grafts are viable and vascularized, and the general structure of the skin (epidermis, adnexa, and dermis) is preserved for at least three months. Visual determination can also be made (e.g., looking for white skin on a black mouse).

EXAMPLE 2

Rat Skin Graft Model

An aqueous-based gel of methylcellulose (Methocel A4M from Dow) is prepared by mixing it in water at a concentration of 20% by weight to give a viscosity useful for a topical skin application. The TGF-$\beta$1 recombinantly produced as described in Example 1 is mixed with the gel to provide a concentration of 1 mg/ml.

This TGF-$\beta$ gel is applied to the lower (back) side of skin taken from F1 Lewis/Brown Norwegian rats. After 24 hours, the skin is placed on the graft bed of the Lewis parent rat, covered with gauze, and then with plaster of Paris, and subsequently removed after ten days. Alternatively, the graft is held in place with metal clips applied using a mechanical clipping device. The results are comparable to those observed for the mice as described above.

EXAMPLE 3

Murine and Rat Islet Cell Transplantation Model

Islet cells are extracted from the pancreas of a BALB/c mouse, soaked in one of the TGF-$\beta$ compositions described in Example 1 for 48 hours, and transplanted into the subrenal capsule space of a streptozotocin-treated allogeneic mouse such as C57BL/6 male mouse. See, e.g., Faustman et al., supra. Similarly, islet cells are extracted from the pancreas of a F1 Lewis/Brown Norwegian rat, incubated in one of the TGF-$\beta$ compositions described in Example 1 for 24–48 hours, and transplanted into the subrenal capsule space of a streptozotocin-treated C57BL/6 mouse. The results indicate that the islet cells are not rejected by the host after three months.

EXAMPLE 4

Murine and Rat Heart Transplant Model

A heart is excised from a sacrificed BALB/c mouse and from a sacrificed F1 Lewis/Brown Norwegian rat. The respective hearts are immediately incubated at room temperature with any of the TGF-$\beta$ solutions of Example 1. The incubations are carried out for 24 to 48 hours. The hearts are washed free of the TGF-$\beta$ solution using two washes of PBS and then immediately transplanted using standard heart transplant operations into the ear of a C3H/HeJ mouse and into the aorta of a F1 Lewis/Brown Norwegian rat from which the hearts had been removed, the mouse heart being received by a different allogeneic strain of mouse and the rat heart being received by a different allogeneic strain of rat. The grafts are not rejected three months after transplantation.

Alternatively, after extraction the heart is stored in a perfluorochemical emulsion such as Fluosol-DA 20% (Green Cross, Japan) to which one of the TGF-$\beta$ solutions is added prior to transplantation in an amount sufficient to provide at least 1 ng/ml of TGF-$\beta$ in the final emulsion.

What is claimed is:

1. A method for the treatment of a graft prior to transplantation comprising:
    pre-treating the graft with a composition comprising a therapeutically effective amount of transforming growth factor-$\beta$ (TGF-$\beta$); and
    transplanting the graft into a compatible host.

2. The method of claim 1 wherein the graft is tissue.

3. The method of claim 1 wherein the graft is skin.

4. The method of claim 3 wherein the treatment comprises coating the lower surface of the skin with the composition.

5. The method of claim 4 wherein the composition comprises a polysaccharide.

6. The method of claim 1 wherein the graft comprises isolated cells.

7. The method of claim 6 wherein the graft comprises islet cells.

8. The method of claim 1 wherein the graft is an organ.

9. The method of claim 8 wherein the organ is selected from group consisting of heart, liver, spleen, pancreas, thyroid lobe, lung, kidney, intestine, blood vessel, and esophagus.

10. The method of claim 1 wherein the host is a mammal.

11. The method of claim 10 wherein the mammal is a human and the graft is derived from a human donor.

12. The method of claim 1 wherein the TGF-$\beta$ is human TGF-$\beta$.

13. The method of claim 12 wherein the TGF-$\beta$ is TGF-$\beta_1$, TGF-$\beta_2$ or TGF-$\beta_3$.

14. The method of claim 1 wherein the treating step takes place in vitro for at least about one minute.

15. The method of claim 1 wherein the treating step takes place in vitro for from about one minute to about 72 hours.

16. The method of claim 1 wherein the composition further comprises a therapeutically effective amount of an immunosuppressive agent that suppresses cytokine production, downregulates or suppresses self-antigen expression, or masks the MHC antigens.

17. The method of claim 16 wherein the immunosuppressive agent is a 2-amino-6-aryl-5-substituted pyrimidine, glutaraldehyde, azathioprine, bromocryptine, cyclophosphamide, antiidiotypic antibodies for major histocompatibility complex antigens, cyclosporin A, a steroid, anti-interferon-$\gamma$ antibodies, anti-tumor necrosis factor-$\alpha$ antibodies, anti-interleukin-2 antibodies, anti-cytokine receptor antibodies, anti-tumor necrosis factor-$\beta$ antibodies, anti-Ia antibodies, heterologous anti-lymphocyte globulin, pan-T antibodies, antibodies to CD4, streptokinase, streptodornase, or RNA or DNA from the host.

18. The method of claim 17 wherein the immunosuppressive agent is cyclosporin A, a glucocorticosteroid, OKT-3 monoclonal antibody, azathioprine, bromocryptine, heterologous anti-lymphocyte globulin, or a mixture thereof.

19. The method of claim 1 wherein the composition is acidic.

20. The composition of claim 19 wherein the pH of the composition is about 4 to about 6.

21. The method of claim 1 wherein the composition is a perfluorochemical emulsion of the TGF-$\beta$.

22. The method of claim 1 further comprising, after the treatment step and before the transplantation step, the step of washing the graft free of the composition.

23. The method of claim 1 wherein the therapeutically effective amount is 1 pg/ml to 1 mg/ml.

24. The method of claim 1 wherein the host undergoes a donor-specific blood transfusion or total lymphoid irradiation before the transplantation.

25. The method of claim 11 wherein the donor of the graft and the host are matched for HLA class II antigens.

26. The method of claim 25 wherein the host undergoes a donor-specific blood transfusion or total lymphoid irradiation before the transplantation.

27. The method of claim 1 further comprising the step of administering to the host after the transplantation a therapeutically effective amount of an immunosuppressive agent that suppresses cytokine production, downregulates or suppresses self-antigen expression, or masks the MHC antigens.

28. The method of claim 26 further comprising the step of administering to the host after the transplantation a therapeutically effective amount of an immunosuppressive agent that suppresses cytokine production, downregulates or suppresses self-antigen expression, or masks the MHC antigens.

29. The method of claim 27 wherein the immunosuppressive agent is TGF-$\beta$, a 2-amino-6-aryl-5-substituted pyrimidine, glutaraldehyde, azathioprine, bromocryptine, cyclophosphamide, antiidiotypic antibodies for major histocompatibility complex antigens, cyclosporin A, a steroid, anti-interferon-$\gamma$ antibodies, anti-tumor necrosis factor-a antibodies, anti-interleukin-2 antibodies, anti-cytokine receptor antibodies, anti-tumor necrosis factor-$\beta$ antibodies, anti-Ia antibodies, heterologous anti-lymphocyte globulin, pan-T antibodies, antibodies to CD4, streptokinase, streptodornase, or RNA or DNA from the host.

30. The method of claim 29 wherein the immunosuppressive agent is TGF-$\beta$, cyclosporin A, a glucocorticosteroid, OKT-3 monoclonal antibody, azathioprine, bromocryptine, heterologous anti-lymphocyte globulin, or a mixture thereof.

31. The method of claim 27 wherein the host is continuously infused with the immunosuppressive agent.

32. The method of claim 27 wherein pulse infusions of the immunosuppressive agent are administered to the host.

33. The method of claim 32 wherein the pulse infusions are carried out using declining doses of the immunosuppressive agent.

34. The method of claim 1 wherein the graft is transplanted into a mammalian species different from that from which the original graft was derived.

35. The method of claim 34 wherein the graft is transplanted into a human and was derived from a mammalian species other than human.

36. The method of claim 1 further comprising, after said treating step and before said transplantation step, the step of storing the treated graft.

37. A graft of living cells, tissue, bone marrow, or organs suitable for transplantation into a recipient host treated with a composition comprising TGF-$\beta$.

38. The graft of claim 37 wherein the composition further comprises an immunosuppressive agent that suppresses cytokine production, downregulates or suppresses self-antigen expression, or masks the MHC antigens.

39. The graft of claim 38 wherein the immunosuppressive agent is a 2-amino-6-aryl-5-substituted pyrimidine, glutaraldehyde, azathioprine, bromocryptine, cyclophosphamide, antiidiotypic antibodies for major histocompatibility complex antigens, cyclosporin A, a steroid, anti-interferon-$\gamma$ antibodies, anti-tumor necrosis factor-a antibodies, anti-interleukin-2 antibodies, anti-cytokine receptor antibodies, anti-tumor necrosis factor-$\beta$ antibodies, anti-Ia antibodies, heterologous anti-lymphocyte globulin, pan-T antibodies, antibodies to CD4, streptokinase, or streptodornase.

40. The graft of claim 39 wherein the immunosuppressive agent is cyclosporin A, a glucocorticosteroid, OKT-3 monoclonal antibody, azathioprine, bromocryptine, heterologous anti-lymphocyte globulin, or a mixture thereof.

41. The graft of claim 38 wherein the composition is acidic.

42. The graft of claim 37 that is skin, wherein the lower surface of the skin to be applied to a host is coated with the composition.

43. The graft of claim 42 wherein the composition comprises a polysaccharide.

44. The graft of claim 37 wherein the composition is a perfluorochemical emulsion.

45. The graft of claim 37 wherein the graft is perfused with the composition.

46. The graft of claim 37 that is derived from a mammal.

47. The graft of claim 46 that is derived from a human.

48. The graft of claim 37 wherein the TGF-$\beta$ is human TGF-$\beta$.

49. The graft of claim 37 wherein the TGF-$\beta$ is TGF-$\beta_1$, TGF-$\beta_2$ or TGF-$\beta_3$.

50. A composition comprising TGF-$\beta$ in a perfluorochemical emulsion.

51. The method of claim 1 wherein the TGF-$\beta$ is TGF-$\beta_1$.

52. The graft of claim 37 wherein the TGF-$\beta$ is TGF-$\beta_1$.

53. The composition of claim 50 wherein the TGF-$\beta$ is TGF-$\beta_1$.

* * * * *